United States Patent
Wolf

(10) Patent No.: US 7,159,443 B2
(45) Date of Patent: Jan. 9, 2007

(54) SIMPLE DISSOLVED CARBON DIOXIDE ANALYZER

(76) Inventor: Peter A. Wolf, 352 Little Quarry Rd., Gaithersburg, MD (US) 20878

( * ) Notice: Subject to any disclaimer, the term of this patent is extended or adjusted under 35 U.S.C. 154(b) by 668 days.

(21) Appl. No.: 10/094,818

(22) Filed: Mar. 12, 2002

(65) Prior Publication Data

US 2003/0172715 A1 Sep. 18, 2003

(51) Int. Cl.
G01N 7/00 (2006.01)
G01N 33/18 (2006.01)

(52) U.S. Cl. .................. 73/19.1; 73/19.01; 73/19.06
(58) Field of Classification Search ................ 73/19.01, 73/19.06, 19.1
See application file for complete search history.

(56) References Cited

U.S. PATENT DOCUMENTS

| 3,782,170 | A | * | 1/1974 | Cramer | 73/19.1 |
| 3,811,841 | A | * | 5/1974 | Kassel | 324/71.4 |
| 4,129,029 | A | * | 12/1978 | Moll et al. | 73/19.06 |
| 4,168,624 | A | * | 9/1979 | Pichon | 73/19.01 |
| 4,739,647 | A | * | 4/1988 | Monticelli, Jr. | 73/23.2 |
| 5,235,843 | A | * | 8/1993 | Langhorst | 73/19.1 |
| 5,861,755 | A | * | 1/1999 | Moerk et al. | 73/19.1 |
| 6,138,497 | A | * | 10/2000 | Nix et al. | 73/19.06 |

FOREIGN PATENT DOCUMENTS

| RU | 1061039 | * | 12/1983 | 73/19.1 |
| RU | 1181379 | * | 2/1986 | 73/19.1 |
| RU | 1693459 | * | 11/1991 | 73/19.1 |

* cited by examiner

Primary Examiner—Daniel S. Larkin

(57) ABSTRACT

The present invention relates to a new concept in measuring the dissolved gas levels in supersaturated liquid streams. In particular, the new device is specifically applicable to the measurement of carbonation levels in soft drinks. The measurement is made by permitting the beverage to escape from the pressurized container to atmospheric pressure through a thin tubing. The gas escaping from the supersaturated beverage separates the liquid stream into alternating gas and liquid segments. The relative long term average length of the segments is directly related to the CO2 content of the beverage. The instrument is simple to operate, inexpensive, and needs no calibration; it is easily adaptable to presently used laboratory equipment, and is useful in production process control.

2 Claims, No Drawings

SIMPLE DISSOLVED CARBON DIOXIDE ANALYZER

BACKGROUND OF THE INVENTION

The level of carbonation is a key property of a variety of soft drinks, as well as of some other beverages, such as champagne and seltzer water. The carbonation level is one of the principal attributes that relates to consumer acceptance and preference, thus, it is carefully monitored during beverage production, and in the trade.

The measurement and control of carbonation level, however, is not very easily accomplished primarily because the measurement has to be performed at pressures considerably higher than ambient; pressures in beverage bottles and cans are typically several atmospheres above atmospheric, depending on the temperature of the beverage.

Carbon dioxide ($CO_2$) is relatively highly soluble in water compared to gases such as nitrogen ($N_2$) or oxygen ($O_2$), however, in order to produce acceptable soft drinks, or champagne for that matter, the solvent (primarily water ($H_2O$) has to be supersaturated with $CO_2$.

Now, $CO_2$ solubility in water (or of any gas in any solvent) is governed by Henry's Law, which simply states that the solubility of the gas is directly proportional to the PARTIAL PRESSURE of the gas above the liquid. The proportionality constant relating the $CO_2$ partial pressure to the solubility is called the Henry's Law constant, and is considerably temperature dependent. In order to achieve the required carbonation level of soft drinks, the $CO_2$ partial pressure has to be raised to several atmospheres. Indeed, the release of this pressure from the container at the time of beverage consumption causes the sudden release of $CO_2$ in the form of bubbles, which is believed to be related to the tingling, somewhat painful, never-the-less pleasing taste of the beverage.

It is a relatively simple matter to measure the $CO_2$ level in a pure liquid in any reasonably well equipped analytical laboratory. For example, one may titrate the $CO_2$ with a base (utilizing its acidic nature), or measure its Infra Red (IR) absorption, or separate and measure the gas from the liquid by means of a gas chromatograph, just to name a few. In an industrial environment, however, some of these methods are not suitable for a number of reasons, such as cost, speed, ease of operation, just to name a few.

Historically, the beverage industry relied on the method, implied by the above mentioned Henry's Law, namely, the measurement of temperature (T) and pressure (P). Since there is a direct relationship between the partial pressure of $CO_2$ and its beverage concentration, at any given temperature, it is a simple matter to develop a look-up table of carbonation levels; one axis of this table is the temperature, the other the pressure, and the table values represent the carbonation levels in some convenient units. An early example of such a chart, widely used by the beverage industry, was the Heath Chart.

The $CO_2$ content of the beverage is typically expressed in units of VOLUMES (VOL), which is a misnomer; it is actually a dimensionless unit, namely, it is the ratio of the volume of gas dissolved per unit volume of liquid. Of course, gases are compressible, and the gas volume is typically expressed at 0 degrees Celsius. Thus, for example, a beverage containing 3 VOLUMES of $CO_2$ at say 25 deg C., would contain 3 liters of $CO_2$ (expressed at 0 deg C.) in 1 liter of beverage at 25 deg C.

A typical measurement is made, by placing the beverage container into a puncturing device, shaking the sample to facilitate the equilibration of $CO_2$ between the headspace and the beverage, followed by the measurement of P and T. The value of the $CO_2$ concentration is then found from the look-up table (or calculated from an equation which expresses the temperature and pressure dependence of Henry's Law).

The Heath chart has been improved upon over the years, and different charts have been developed for different beverages, as the solubility of $CO_2$ in them varies, primarily due to dissolved sugar.

There is, however, a rather important problem with the whole method of P and T measurement, and the $CO_2$ VOLUMES obtained from them. It was mentioned earlier that the concentration of $CO_2$ is related to the PARTIAL PRESSURE of $CO_2$. The total pressure in a beverage bottle is the sum of the partial pressures of all the gases present. Water vapor contributes slightly, but it can be easily subtracted from the total pressure, as it is well known over a considerable temperature range. A much larger problem is the partial pressure contributed by the small amount of entrapped AIR in the bottle. Even though the amount of air in the bottle is small, its partial pressure is rather large due to its small solubility in (sugar) water. The amount of air in a bottle can be measured, with difficulty, but its contribution to the partial pressure is a complicated function of beverage and headspace volume, as well as of temperature.

Rather than correcting for the presence of air, a relatively clever trick is used to minimize its effect. Prior to $CO_2$ measurement, the headspace pressure is quickly released; a process called SNIFTING. The rationale is that, since the solubility of air in the beverage is small, the air is primarily in the headspace, thus SNIFTING results in the loss of most of the air from the container. Subsequent measurement of the pressure can be taken to be that of $CO_2$ only. This assumption is fairly good, and rather precise measurements of $CO_2$ concentration can be made (within 1 to 2%) if the snifting is done with care. However, as anyone who opened a soft drink container knows, as the container is opened, usually some $CO_2$ escapes as well, as can easily be seen from the evolution of bubbles from the beverage. Thus, more than just the air escapes. The amount of $CO_2$ that escapes depends on a number of variables: beverage type, container type, temperature, history of the sample, relative headspace, and beverage volume, etc. Thus, the error introduced by snifting can easily be as large as 10% of the measurement. The analyst is confronted with the error caused by the presence of air, or the error caused by the snifting procedure.

A number of more sophisticated instrumental methods have been transplanted from the analytical laboratory to the beverage production platform, for example methods using IR absorption, and gas chromatography. Also, an interesting procedure was suggested using gas permeable membranes (Szerenyi et. al. U.S. Pat. No. 4,517,135). None of these methods have found wide acceptance in the beverage industry for a variety of reasons, notably cost, analysis time, and ease of universal adaptability; the beverage industry still prefers the simple P and T measurement method despite its shortcoming, principally due to the confounding effect of air.

SUMMARY OF THE INVENTION

Concept

Suppose a thin (stainless steel) tube is inserted into a pressurized container of beverage and permits the contents of the beverage to escape slowly through the tube, and exiting to the outside at ambient (nearly one atmosphere) pressure. If the tube is connected to a thin plastic tubing, it is readily observed that the initially foaming liquid gradually coalesces into alternating segments of liquid and gas with easily discernible menisci separating them. The alternating segments of liquid and gas are of irregular lengths that vary depending on beverage type, carbonation level, flow rate, etc.

If, however, the lengths of liquid and gas segments are each added and accumulated for a suitable period of time, they approach a constant ratio. In other words, the long term average of the distribution of lengths of the both type of segments approach constant values, and the ratio of the average (or total) lengths of the gas and liquid segments approach a constant value indicative of the $CO_2$ content of the beverage. The approach of the average segment lengths to constant values is indicative of the equilibration of $CO_2$ between the gas and liquid phases, and is made possible, in a relatively short length of tubing, by the high interfacial area between the segments through which the transport of $CO_2$ from the liquid to the gas phase takes place. The equilibration of $CO_2$ between the gas and liquid phase is easily substantiated by quantitative experiments, for example by the introduction of a known weight of sodium bicarbonate and excess acid into a closed beverage bottle. When such a sample is analyzed by this new method, it yields precisely the average gas and liquid segment lengths predicted.

During the process of the flow through the thin tube, the beverage looses the excess $CO_2$ from the beverage, and the gas segments equilibrate with the liquid at ambient (nearly one atmosphere) pressure. The total $CO_2$ content of the beverage is the sum of what is contained in the gas segments plus what remains in the beverage near the exiting ambient (near one atmosphere) pressure. The average gas and liquid segment lengths are easily measured, and what is left in the beverage, in equilibrium with the ambient pressure is easily established by prior measurement via an independent laboratory procedure, and is known once and for all. This procedure offers a very simple method for analyzing the $CO_2$ content of the beverage; one simply measures the relative average lengths of the gas and liquid segments, and then adds the previously determined value of the $CO_2$ content of the beverage at ambient pressure.

The flow of alternating gas and liquid segments in a thin tube resembles, in its physical state, the flow of gas and liquid segments in an analytical chemical procedure known as Segmented Flow Analysis (SFA). During SFA, a continuous liquid stream is intentionally broken up into short segments of equal length by the injection of a foreign, typically inert (non-reactive), gas at periodic intervals. The purpose is to form small isolated packets of liquid, so that chemical or physical measurements may be performed on them. Occasionally, some gas, if contained in the liquid segments, may escape into the neighboring gas segments, and may permit quantitative testing.

The newly proposed, novel, carbonation testing has nothing in common with SFA, and is not derived from it. The invention derives from the observation that under controlled release of beverage from a highly carbonated beverage into a thin tube, exiting to ambient pressure, alternating gas and liquid segments, of irregular and unequal lengths, are formed. No chemical or physical measurements are performed or required. Rather, the relative average lengths of the gas and liquid segments is sought, and it is this ratio of lengths that is related to the quantity of $CO_2$ that was originally dissolved in the beverage.

Measurement

The simplest way to measure the average relative length of the gas and liquid segments is to weigh the tubing. First the tubing is tared on a suitable balance to the precision desired, then prepare a calibration plot of the tared tubing with two fixed points: the tubing completely empty, and then completely full of un-carbonated beverage. The average relative length of the gas and liquid segments is found on the straight line connecting the two calibration points.

There is a much more elegant way to proceed, however. If one inserts two thin metal wires through the wall of the tubing opposite each other, so that they just barely protrude through the inside wall, and connects it to a suitable electrical circuit, then the voltage, current, or resistance (depending on how the electrical circuit is designed) will be observed to change sharply as alternating liquid or gas segments flow past the electrodes, as there is a very large difference in the electrical conductivity between the two type of segments. The output of the electrical circuit is essentially a square wave of varying lengths. The lengths of the half-waves, i.e. when the voltage (or current) is high, or when it is low, can be measured using an oscillator of suitable fixed frequency by simply counting the number of oscillations between the successive changes of voltage (or current) from low to high or vice versa. The particulars of the electrical circuitry is not of any interest here, as it can be easily designed by electrical engineers trained in this field, and is not considered as part of this invention. Suffice it to say, the square-wave output at the electrodes can easily be measured, and the average duration of the low and high voltages (currents) easily recorded.

There are added benefits to this kind of electrical monitoring of the segment lengths. Recall that the VOLUMES of carbonation is a relative number, i.e. It is expressed as a ratio of $CO_2$ volume to beverage volume. That means that we only need to measure the relative volumes of the gas and liquid segments flowing in the tubing. As the tubing cross section at the electrodes doesn't change, we need to measure their relative lengths, which means that we have to measure the relative lengths of the electrical pulses of the square-wave. Provided that the flow rate of the gas and liquid segments is constant during the measurement, the above relative lengths of the two segments is directly related to the $CO_2$ VOLUMES. Furthermore, provided the reference frequency of the oscillator that measures the lengths of the segments doesn't change during the measurement, which takes about one minute, no calibration is necessary.

Therefore, this innovative, and very simple method of measurement easily provides the necessary precision and accuracy, and it needs no calibration.

There are other strategies to measure the gas and liquid segment lengths. As the segments are easily seen by the eye, an optical sensor is also possible. Small optical sensors are readily available, and could replace the electrical sensors without the need to intrude into the inside of the tubing.

Inductive or capacitive detection of the menisci are also possible, although they do not have the fine resolution of the optical and electric sensors.

Measurement Use and Application

In the above discussion frequent reference was made to beverage containers (cans or bottles). This is the most frequent application of carbonation levels. Puncturing devices, which puncture the containers, and permit the P and T measurement currently in use, are readily available. These puncturing devices can be readily adapted to pierce the containers and insert a thin tube through which the beverage can exit. Although the pressure in the container can be used to push the beverage out of the container through a needle valve, it is more reliable to attach a small pressurized tank of some gas ($CO_2$, $N_2$, or other) and force the liquid out at constant pressure, guaranteeing constant flow rate at the detector. Thus, only trivial modification to existing mechanical equipment is needed.

The dimensions of the tubing can vary over a range typically, but not exclusively, from 1/16 in. to 3/16 in. If considerably narrower tubing is used, it will provide an undue friction to the flow, and higher diameter tubing will not support the menisci, so that some longitudinal rather than plug flow of the segments may take place. The proper diameter of the tubing depends on the particular liquid system. The length of tubing required depends on the flow rate selected and on the measurement time required. In any case, the proper combination of flow rate and measurement time is governed by the rate of equilibration of $CO_2$ between the gas and the liquid phases. For the above mentioned diameters, a tubing length of 10 ft. to 20 ft. was found to be adequate.

The tubing may be made of a number of materials, for example glass, metals (e.g. stainless steel), or a variety of plastics. Materials that are wetted by the liquid generally perform better, but are not required.

There are two other situations where this novel measurement technique could prove even more useful. One is the possibility of measuring the carbonation of fountain syrups. Currently this is typically performed using the same P and T measurement discussed above, but preceded by quickly pouring the beverage into a sealable cup from the soft drink fountain. As anyone who obtained beverage from a fountain knows, a considerable and varying amount of $CO_2$ is lost during the pouring, which limits the precise assessment of the carbonation level in the fountain.

The instrument proposed in this invention overcomes this problem by permitting the attachment of the thin tubing directly to the fountain outlet via a simple threaded or other mechanical coupling. This permits not only a precise and simple measurement, but also prevent the loss of any $CO_2$ prior to measurement.

The second application for the new instrument is in monitoring the carbonation level during beverage production. Currently, considerable time elapses during the start-up of a beverage production line before the beverage quality can be established by the current P and T measurement method. During this time many cases of beverage are produced which are not at the quality standards specified. With the use of the new instrument, the carbonation level can be monitored on line during the production by simply monitoring the relative average gas and liquid segments. Thus no, beverage needs to be put in bottles and cans until they reach the correct carbonation level.

Other Uses

Although the focus of the discussion up to this point has been the soft drink industry, the method of measuring gas content in other supersaturated liquid streams by this new method is also possible. If a liquid stream is supersaturated with some gas in any application, the natural tendency for the gas is to escape when the pressure is lowered to a lower pressure. Thus, the liquid stream will tend to produce alternating gas and liquid segments, when allowed to flow through a thin tube that is open to a lower pressure. The segments will typically be of unequal and non uniform length, but the average lengths of each type of segment over a period of time will be constant, and characteristic of that stream.

Thus, the measurement of the segment lengths can be used to accurately measure the gas concentration in the supersaturated stream, and also to monitor it during production.

What is claimed is:

1. An instrument measuring the dissolved gas concentration in supersaturated liquid streams, said instrument consisting of a thin tube, through which the liquid flows, and in which the supersaturated liquid stream breaks up into gas and liquid segments of varying lengths, and a detector that measures the average relative lengths of the gas and liquid segments, where the detector is comprised of electrodes protruding into the tubing containing the gas and liquid segments, and an electronic voltage or current sensing circuit that measures the average relative lengths of the electrical pulses generated by the difference in electrical conductivity between the gas and liquid segments.

2. An instrument measuring the dissolved carbon dioxide gas concentration in supersaturated beverage streams, said instrument consisting of a thin tube, through which the liquid flows, and in which the supersaturated liquid stream breaks up into gas and liquid segments of varying lengths, and a detector that measures the average relative lengths of the gas and liquid segments, where the detector is comprised of electrodes protruding into the tubing containing the gas and liquid segments, and an electronic voltage or current sensing circuit that measures the average relative lengths of the electrical pulses generated by the difference in electrical conductivity between the gas and liquid segments.

* * * * *